(12) United States Patent
Park (10) Patent No.: US 9,334,301 B2
(45) Date of Patent: May 10, 2016

(54) NUCLEIC ACID CONSTRUCT AND METHOD OF PREPARING NANOPARTICLE USING THE SAME

(71) Applicant: SAMSUNG ELECTRONICS CO., LTD., Suwon-si (KR)

(72) Inventor: No-kyoung Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 56 days.

(21) Appl. No.: 13/771,374

(22) Filed: Feb. 20, 2013

(65) Prior Publication Data

US 2013/0310548 A1 Nov. 21, 2013

(30) Foreign Application Priority Data

May 21, 2012 (KR) ........................ 10-2012-0053768

(51) Int. Cl.
| | | |
|---|---|---|
| C07H 23/00 | (2006.01) | |
| C07H 21/00 | (2006.01) | |
| B82Y 5/00 | (2011.01) | |

(52) U.S. Cl.
CPC ................ *C07H 23/00* (2013.01); *C07H 21/00* (2013.01); *B82Y 5/00* (2013.01)

(58) Field of Classification Search
None
See application file for complete search history.

(56) References Cited

U.S. PATENT DOCUMENTS

| 5,948,897 A * | 9/1999 | Sen et al. ..................... 536/22.1 |
|---|---|---|
| 7,923,109 B2 | 4/2011 | Belcher et al. |
| 2010/0048424 A1 | 2/2010 | Kwon |
| 2011/0189483 A1 | 8/2011 | Zubarev et al. |

FOREIGN PATENT DOCUMENTS

| KR | 10-2007-0017319 A | 2/2007 |
|---|---|---|
| KR | 10-0813113 B1 | 3/2008 |
| KR | 10-2011-0080229 A | 7/2011 |
| WO | 98/04740 A1 | 2/1998 |
| WO | 01/51665 A2 | 7/2001 |
| WO | 2008/141289 A1 | 11/2008 |

OTHER PUBLICATIONS

Rothemund (Mar. 16, 2006) "Folding DNA to create nanoscale shapes and patterns", Nature, 440(3): 297-302.*
Heckel, et al. (2008) "Building objects from nucleic acids for a nanometer world", Biochimie, 90: 1096-1107.*
Douglas, et al. (May 21, 2009) "Self-assembly of DNA into nanoscale three-dimensional shapes", Nature, 459: 414-418.*
Swami, et al. (2009) "Phase Transfer of Gold Metallized DNA", Journal of Cluster Science, 20: 281-90.*
European Patent Office, Communication dated Sep. 25, 2013, issued in counterpart European Patent Application No. 13163983.3.
Liu, Jianfei et al., "Metallization of Branched DNA Origami for Nanoelectronic Circuit Fabrication," ACS NANO, vol. 5, No. 3, Feb. 16, 2011, pp. 2240-2247.
Hao et al., "Plasmon Resonances of a Gold Nanostar", Nano Letters, pp. 729-732, vol. 7, No. 3, 2007, American Chemical Society.
Sau et al., "Room Temperature, High-Yield Synthesis of Multiple Shapes of Gold Nanoparticles in Aqueous Solution", JACS Communications, pp. 8648-8649, vol. 126, No. 28, 2004.
Yuan et al., "Shape and SPR Evolution of Thorny Gold Nanoparticles Promoted by Silver Ions", Chem. Mater. pp. 1592-1600, vol. 19, No. 7, 2007, American Chemical Society.
Bakr et al., "High-Yield Synthesis of Multi-Branched Urchin-Like Gold Nanoparticles", Chem. Mater., pp. 3297-3301, vol. 18, No. 14, 2006, American Chemical Society.
Chen et al., "Monopod, Bipod, Tripod, and Tetrapod Gold Nanocrystals", JACS Communications, pp. 16186-16187, vol. 125, No. 52, 2003.
Busbee et al., "An Improved Synthesis of High-Aspect-Ratio Gold Nanorods", Advanced Materials, pp. 414-416, vol. 15, No. 5, Mar. 4, 2003.
Deng et al., "DNA-Templated Fabrication of 1D Parallel and 2D Crossed Metallic Nanowire Arrays", Nano Letters, pp. 1545-1548, vol. 3, No. 11, 2003, American Chemical Society.
Ahmed et al., "Controlling the morphology of multi-branched gold nanoparticles", Nanotechnology, vol. 21, 2010, IOP Publishing, 6 pages.
Seol et al., "Gold nanoparticles: enhanced optical trapping and sensitivity coupled with significant heating", Optics Letters, pp. 2429-2431, vol. 31, No. 16, Aug. 15, 2006.

* cited by examiner

*Primary Examiner* — Robert M Kelly
(74) *Attorney, Agent, or Firm* — Sughrue Mion, PLLC (57) ABSTRACT

A nucleic acid construct, a method of preparing a nanoparticle by using the nucleic acid construct, and a nanoparticle and nanoparticle complex prepared using the method. Various types of metal nanoparticles may be efficiently prepared using the template for preparing a nanoparticle and the nanoparticle prepared using the template.

14 Claims, 4 Drawing Sheets

NUCLEIC ACID CONSTRUCT AND METHOD OF PREPARING NANOPARTICLE USING THE SAME

CROSS-REFERENCE TO RELATED APPLICATIONS

This application claims the benefit of Korean Patent Application No. 10-2012-0053768, filed on May 21, 2012, in the Korean Intellectual Property Office, the disclosure of which is incorporated herein in its entirety by reference.

BACKGROUND

1. Field

The present disclosure relates to nucleic acid construct templates for preparing nanoparticles, methods of preparing nanoparticles using the templates, and nanoparticles and nanoparticle complexes prepared using the methods.

2. Description of the Related Art

The emergence of nanotechnology has led to innovative advances in various technical fields. The field of nanotechnology, for example, encompasses the preparation of desired structures using materials at a scale of nanometers corresponding to the approximate size of a small molecule and the application of the structures to various fields.

Metal nanoparticles have been widely used in bioassays for detecting a single cell and a single molecule by using their photophysical and chemical properties, or in the development of nano-scale biosensors manufactured by applying nanotechnology to existing biosensors. In addition, metal nanoparticles may be suitable to use in assays of protein-protein interactions, interactions between biomolecules, and DNA sequencing by using their surface plasmon absorption properties and their properties of being sensitive to changes in their surroundings. In particular, gold nanoparticles absorb light and convert it to heat, and thus, may be used for the treatment of diseases by disrupting target cells. In addition, palladium or platinum nanoparticles may be used as a chemical catalyst.

Structures and materials of metal nanoparticles are two of the most important factors for determining the physical properties of the metal nanoparticles. Researches for controlling the structure of metal nanoparticles has been actively conducted. Rod-type metal nanoparticles or nanoparticles with an irregularly branched structure are routinely formed by adding a surfactant when a metal ion is reduced.

SUMMARY

Manufacturing of nano-scale structures and nano-scale devices using natural or artificial biomolecules have emerged, and a precise and efficient fabrication of biomolecule structures are disclosed.

Provided are templates for preparing nanoparticles which include at least two single-stranded nucleic acids, methods of preparing nanoparticles by using the templates, and nanoparticles and nanoparticle complexes prepared using the methods.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an exemplary embodiment of the present invention, a template for preparing a nanoparticle includes at least two single-stranded nucleic acids, wherein each of the at least two single-stranded nucleic acids includes at least ten nucleotides and at least two adjacent segments, wherein the segments of one of the at least two single-stranded nucleic acids are substantially complementarily bound respectively to segments of the other single-stranded nucleic acids.

The term "nanoparticle(s)" used herein is intended to mean particles of various shapes, of which width may range from about 1 nm to several tens nm. The nanoparticles may have a longer length than its width, wherein the length may range from a few nm to several hundred nm.

The term "nucleic acid template," "nucleic acid construct," or "nucleic acid template construct," which are sometimes interchangeably used herein, is used to prepare a nanoparticle, and the structure of the nanoparticle may be more precisely controlled using the template. The nucleic acid template, nucleic acid construct, or nucleic acid template construct is an artificially constructed nucleic acid molecule.

The term "nucleic acid" as used herein may be used interchangeably with the term "polynucleotide," and refers to a polymer of deoxyribonucleotide or ribonucleotide. In addition, the polynucleotide includes analogues of natural polynucleotides, unless specifically mentioned. According to an embodiment, the nucleic acid may be selected from the group consisting of deoxyribonucleic acid (DNA), ribonucleic acid (RNA), peptide nucleic acid (PNA), locked nucleic acid (LNA), and analogues thereof, but is not limited thereto.

In one embodiment, the template may include, for example, 2 to 10, 2 to 8, 2 to 6, or 2 to 4 single-stranded nucleic acids.

In one embodiment, the single-stranded nucleic acid may include, for example, 2 to 5, 2 to 4, or 2 to 3 segments.

The term "segment" as used herein refers to a portion of polynucleotides included in the single-stranded nucleic acid. The single-stranded nucleic acid may include at least two segments, and the at least two segments may be oligonucleotides having different sequences. In addition, the segments of the single-stranded nucleic acid may substantially complementarily bind to segments of the other single-stranded nucleic acid. The segments within a same nucleic acid may be separated from each other by 1-3 nucleotides or be contiguous to each other.

The term "substantially complementary," or "substantially complementarily bind(ing)" or "substantially complementary bound" used herein indicates that two different polynucleotides are hybridized under stringent conditions known in the art. The stringent conditions may be determined by adjusting a temperature, an ionic strength (buffer concentration), the presence of a compound such as an organic solvent or the like, and may vary according to a sequence to be hybridized. For example, the stringent conditions may be a) washing with 0.015 M sodium chloride/0.0015 M sodium citrate/0.1% sodium dodecyl sulfate at 50° C.; or b) hybridizing in a hybridization buffer (including 50% formamide, 2×SSC and 10% dextran sulfate) at 55° C. and then washing with EDTA-containing 0.1×SSC at 55° C.

Various shapes of oligonucleotide or nucleic acid template constructs for preparing nanoparticles may be prepared by varying the number of the single-stranded nucleic acids and the number of the segments of each single-stranded nucleic acid. For example, a linear template construct for preparing a nanoparticle may be prepared using complementary two single-stranded nucleic acids in which two segments of one of the two single-stranded nucleic acids are arranged adjacent to two segments of the other thereof without a linker (e.g., FIG. 1(C)). Alternatively, a Y-shaped template construct (FIG. 1(A)) may be prepared using three single-stranded nucleic acids each having two segments, or an X-shaped template construct (FIG. 1(B)) for preparing a nanoparticle may be prepared using four single-stranded nucleic acids each having two segments.

According to an embodiment, the template construct may include at least one member which improves the stability of the construct. For example, the complementary strands of the nucleic acids may be cross-linked to each other. In an embodiment, an intercalator may be used. Intercalators may include, but is not limited to, a fluorescent intercalator selected from the group consisting of YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium bromide, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes, and 7-aminoactinomycin D. In another embodiment, psoralen or its derivatives, proflavine, daunomycin, doxorubicin, or thalidomide may be used.

In an exemplary embodiment, a cross-linking between two complementary strands of the nucleic acid by way of an intercalator may be chemically induced by intercalating psoralen into a complementary double-stranded nucleic acid and then irradiating an ultraviolet ray A thereto to form a covalent bond between bases of the nucleic acid.

According to one embodiment, the adjacent segments may not include a linker or may further include a linker consisting of 1 to 50 nucleotides that do not complementarily bind to any one of the at least two single-stranded nucleic acids. That is, the linker may link the at least two adjacent segments of each single-stranded nucleic acid to each other, and unlike the segments described above, the linker does not complementarily bind to any one of the single-stranded nucleic acids, whereby a more flexible template for preparing a nanoparticle may be obtained.

According to another embodiment of the present invention, there is provided a nanoparticle in which a metal ion or a metal precursor is bound to the template construct. The metal ion or metal precursor is bound to a backbone of the template construct bases in nucleic acids.

As described above, the template for preparing a nanoparticle is a double-stranded polynucleotide in which at least two single-stranded nucleic acids substantially complementarily bind to each other, and thus, the template has a negatively charged phosphate backbone. Thus, positively charged metal ions bind to the phosphate backbone by electrical attraction, whereby a nanoparticle having the same shape as that of the template for preparing a nanoparticle may be formed. Also, a specific metal precursor may bind to bases of the nucleic acid. In this case, the metal precursor binds in the same manner as in the binding by electrical attraction to correspond to the shape of a template for the nucleic acid and as a result, a nanoparticle with the same shape as that of the nucleic acid template may be formed.

In an exemplary embodiment, a metal may be selected from the group consisting of gold (Au), silver (Ag), copper (Cu), platinum (Pt), palladium (Pd), and combinations thereof, but is not limited thereto.

According to another embodiment of the present invention, a nanoparticle complex includes at least two of the nanoparticles, in which an end of one of the at least two of the nanoparticles is bound to an end of the other nanoparticle. According to an embodiment, a nanoparticle complex in which one Y-shaped Au nanoparticle is bound to another Y-shaped Ag nanoparticle may be formed by preparing the Y-shaped Au nanoparticle and the Y-shaped Ag nanoparticle by using the respective template DNA constructs and binding an end of the Au nanoparticle to an end of the Ag nanoparticle. Alternatively, a nanoparticle complex composed of different metals may be formed by binding different metal precursors to the template DNA constructs, binding ends of the templates to each other, and reducing the resultant templates.

According to another embodiment of the present invention, a method of preparing a nanoparticle includes mixing at least two single-stranded nucleic acids each including at least ten nucleotides and at least two adjacent segments, wherein the segments of one of the at least two single-stranded nucleic acids are substantially complementarily bound respectively to segments of the other single-stranded nucleic acid(s) so as to be hybridized; adding a stabilizer such as an intercalator to the hybridized resultant to form cross-linking between the single-stranded nucleic acids or stabilize a double-stranded nucleic acid formed by the hybridization of the single-stranded nucleic acids to prepare a nucleic acid template; and contacting the nucleic acid template with a metal ion to form a nanoparticle having the same shape as that of the nucleic acid template.

The method of preparing a nanoparticle will now be described in more detail.

First, the method may include mixing at least two single-stranded nucleic acids each including at least ten nucleotides and at least two adjacent segments, wherein the segments of one of the at least two single-stranded nucleic acids are substantially complementarily bound respectively to segments of the other single-stranded nucleic acids so as to be hybridized and adding a stabilizing agent, such as an intercalator to the hybridized resultant to form cross-linking between the single-stranded nucleic acids or to stabilize a double-stranded nucleic acid formed by the hybridization of the single-stranded nucleic acids to prepare a nucleic acid template.

These steps have already been described above in the description of the process of preparing a template construct, and types of the at least two single-stranded nucleic acids, the number of the single-stranded nucleic acids, and the segments have also already been described above, and thus, a detailed description thereof will not be repeated here to avoid making the specification overly complex.

The segments of one of the at least two single-stranded nucleic acids each include a base sequence, which enables the segments to hybridize to substantially complementary segments of the other single-stranded nucleic acids, and thus, the hybridizing step may be performed by considering a Tm value of the at least two single-stranded nucleic acids such that a hybridization spontaneously occurs at a temperature lower than the Tm value.

In addition, as described above, to improve stability of the resulting complementary double stranded structure, an stabilizing agent such as an intercalator is added to the hybridized resultant. The intercalator may form a cross-linking between the non-hybridized single-stranded nucleic acids or stabilize a double-stranded nucleic acid obtained by the hybridization. According to an embodiment, the intercalator may be selected from the group consisting of psoralen and a derivative thereof, ethidium bromide, proflavine, daunomycin, doxorubicin, and thalidomide, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes, and 7-aminoactinomycin D, but is not limited thereto.

As a last step, the method may include contacting the nucleic acid template with a metal ion or a metal precursor and adding a reducing agent thereto.

In one embodiment, the metal ion may be, for example, a metal ion or a metal precursor selected from the group consisting of Au, Ag, Cu, Pt, Pd, and combinations thereof, but is not limited thereto.

The prepared nucleic acid template includes phosphate backbones, and thus being negatively charged. Thus, by contacting the nucleic acid template with metal ions, maintaining the resultant structure for a period of time sufficient to induce binding between the nucleic acid and the metal ions, removing metal ions that are not bound to the nucleic acid template construct, and adding a reducing agent to the resulting product, the metal ion is reduced to a metal and the metal is disposed on the nucleic acid template construct, thereby forming a nanoparticle having the substantially same shape as that of the nucleic acid template. Alternatively, a nanoparticle having the same shape as that of the nucleic acid template may be formed by contacting the nucleic acid template with a metal precursor binding to bases of the nucleic acid and reducing the resultant structure.

One or more embodiments of the present invention will now be described more fully with reference to the following examples. However, these examples are provided only for illustrative purposes and are not intended to limit the scope of the present invention.

Figure 1:
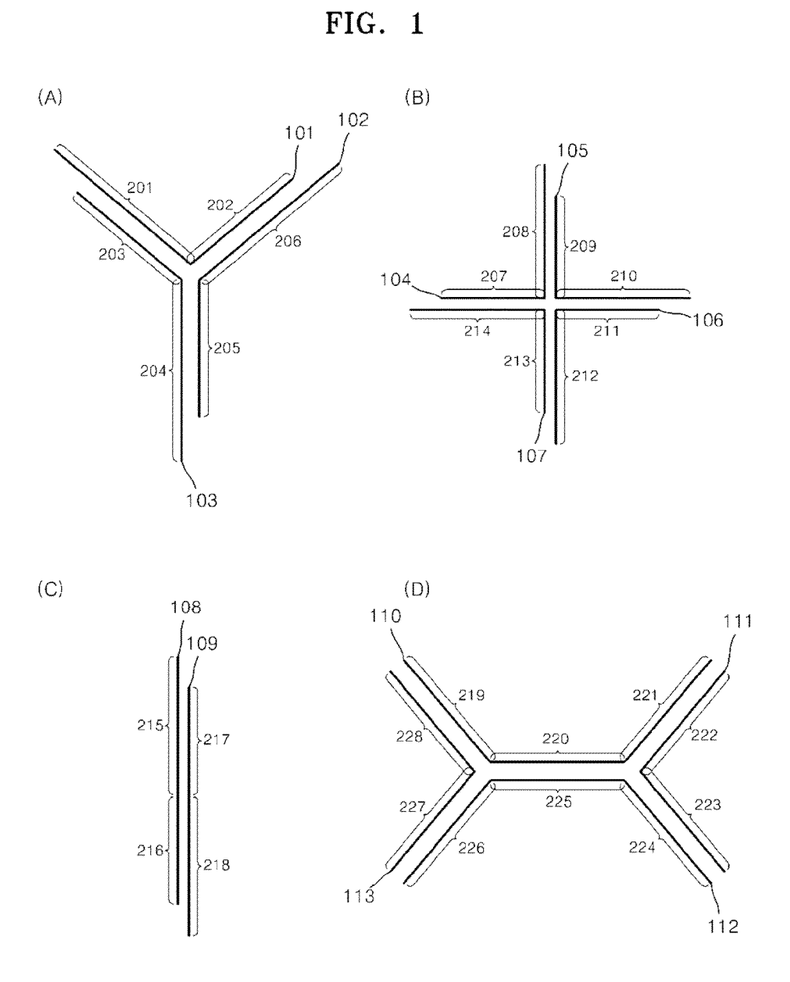
FIGS. 1A through 1D illustrate various types of nucleic acid templates for preparing nanoparticles, according to exemplary embodiments of the present invention.

FIGS. 1A through 1D illustrate various types of nucleic acid templates for preparing a nanoparticle, according to an exemplary embodiment of the present invention. FIG. 1A illustrates a Y-shaped nucleic acid template including three single-stranded nucleic acids 101, 102 and 103 including two segments 201 and 202, two segments 205 and 206, and two segments 203 and 204, respectively. FIG. 1B illustrates an X-shaped nucleic acid template including 4 single-stranded nucleic acids 104, 105, 106 and 107 including two segments 207 and 208, two segments 209 and 210, two segments 211 and 212, and two segments 213 and 214, respectively. As illustrated in FIG. 1A or 1B, segments of one of a plurality of single-stranded nucleic acids are bound or hybridized to their respective substantially complementary segments of the other single-stranded nucleic acids thereby forming the Y-shaped nucleic acid template (by complementary binding between segments 201 and 203, between 202 and 206, and between 204 and 205) or the X-shaped nucleic acid template (by complementary binding between 208 and 209, between 210 and 211, between 212 and 213, and between 214 and 207).

FIG. 1C illustrates a 1-shaped nucleic acid template including two single-stranded nucleic acids 108 and 109 including two segments 215 and 216 and two segments 217 and 218, respectively. In an embodiment, at least two of the 1-shaped nucleic acid templates may be formed as an 11-shaped nucleic acid template. FIG. 1D illustrates a dumbbell-shaped nucleic acid template including a single-stranded nucleic acid 110 including segments 219, 220 and 221, a single-stranded nucleic acid 111 including segments 222 and 223, a single-stranded nucleic acid 112 including segments 224, 225 and 226, and a single-stranded nucleic acid 113 including segments 227 and 228. As illustrated in FIG. 1C or 1D, segments included in one of a plurality of single-stranded nucleic acids are bound or hybridized to their respective substantially complementary segments of the other single-stranded nucleic acids, thereby forming the 1-shaped nucleic acid template (by complementary binding between 215 and 217 and between 216 and 218) or the dumbbell-shaped nucleic acid template (by complementary binding between segments 219 and 228, between 220 and 225, between 221 and 222, between 223 and 224, and between 226 and 227).

The Y-shaped, X-shaped, 1-shaped and dumbbell-shaped nucleic acid templates are provided only for illustrative purposes, and various types of nucleic acid templates may be formed according to the number of the single-stranded nucleic acids and the number of the segments of each single-stranded nucleic acid. In addition, metal nanoparticles with various shapes such as the letter Y, letter X, number 1 and a dumbbell may be prepared using the nucleic acid templates described above.

EXAMPLE 1

Preparation of Y-Shaped Nucleic Acid Template for Preparing Nanoparticle

Figure 2:
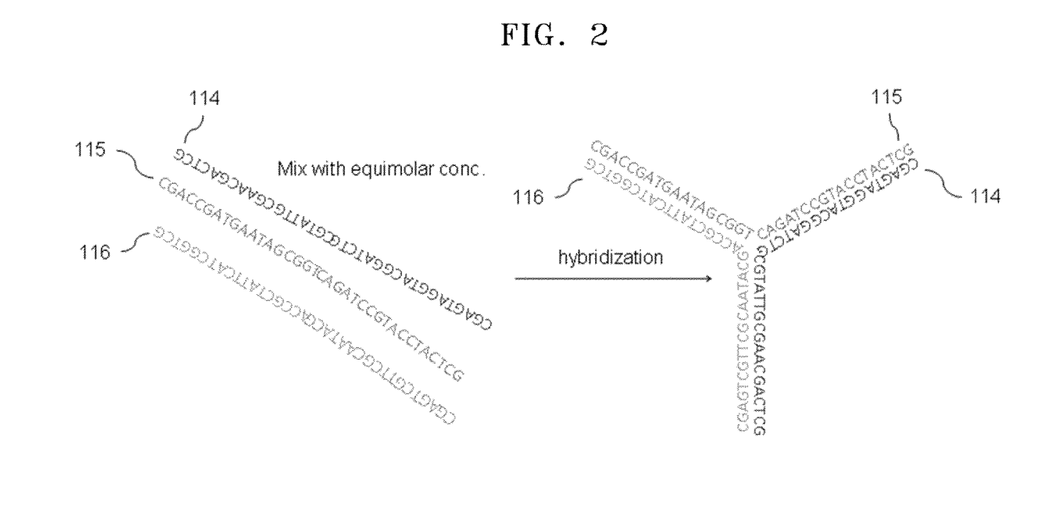
FIG. 2 illustrates a method of forming a Y-shaped nucleic acid template, according to an exemplary embodiment of the present invention.

Polynucleotides with sequences of SEQ ID NOS: 1 to 3 produced by Integrated DNA Technologies, Inc were mixed together at the same concentration (0.1 mM each) and subjected to a hybridizing process to prepare a Y-shaped nucleic acid template for preparing a nanoparticle. FIG. 2 is a diagram for explaining a method of forming a Y-shaped nucleic acid template. The hybridizing process was performed as follows:

The mixed polynucleotides were maintained at 95° C. for 2 minutes; at 65° C. for 2 minutes; at 60° C. for 5.5 minutes; and at 1° C. for 30 seconds. This process was repeatedly performed to make the temperature of the mixed polynucleotides reach 20° C. Then, the temperature thereof was lowered to 4° C., thereby completing the hybridizing process. The resultant polynucleotides were stored at 4° C. or −20° C. before being used to prepare a nanoparticle.

The hybridizing process was performed in a 1×TE (pH 8.0) buffer, and if desired, NaCl was added to the buffer to make the concentration of the resultant buffer reach 100 mM. The temperature adjustment was implemented using a thermal cycler (Eppendorf).

Figure 3:
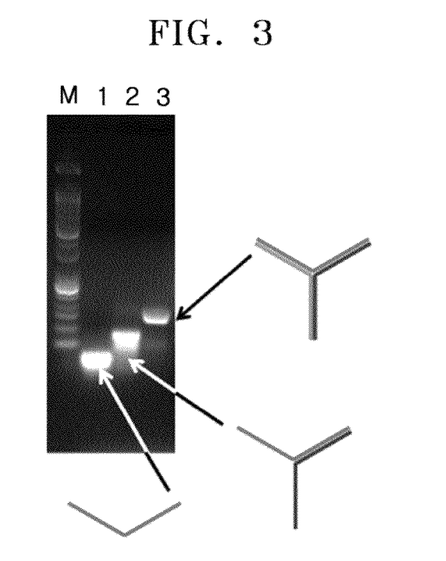
FIG. 3 illustrates electrophoresis results which confirm a Y-shaped nucleic acid template prepared according to an embodiment of the present invention (M: the marker lane, 1: lane 1, 2: lane 2, 3: lane 3)

The prepared nucleic acid template for preparing a nanoparticle was performed by electrophoresis. As illustrated in FIG. 3, it was confirmed that a Y-shaped hybridized polynucleotide (Lane 3) was formed from the polynucleotides having the base sequences of SEQ ID NOS: 1 to 3 through the processes described above. In FIG. 3, Lane 1 denotes the single-stranded polynucleotide having the base sequence of SEQ ID NO: 1, and Lane 2 denotes a polynucleotide in which one segment of the single-stranded polynucleotide having the base sequence of SEQ ID NO: 1 was hybridized with one segment of the polynucleotide having the base sequence of SEQ ID NO: 2.

EXAMPLE 2

Preparation of Nucleic Acid Template for Preparing Nanoparticle in Which Cross-Linking is Formed Between Nucleic Acid Strands The Y-shaped nucleic acid template construct prepared according to Example 1 and psoralen were mixed at a molar concentration ratio of 1:100 and then stirred for 1 hour, and UV having a wavelength of 365 nm was irradiated thereto. Subsequently, unreacted psoralen was filtered and removed from the mixture, and polynucleotide with psoralen bound thereto was suspended in distilled water, thereby completing the preparation of a nucleic acid template for preparing a nanoparticle, with cross-linking between nucleic acid strands.

Figure 4:
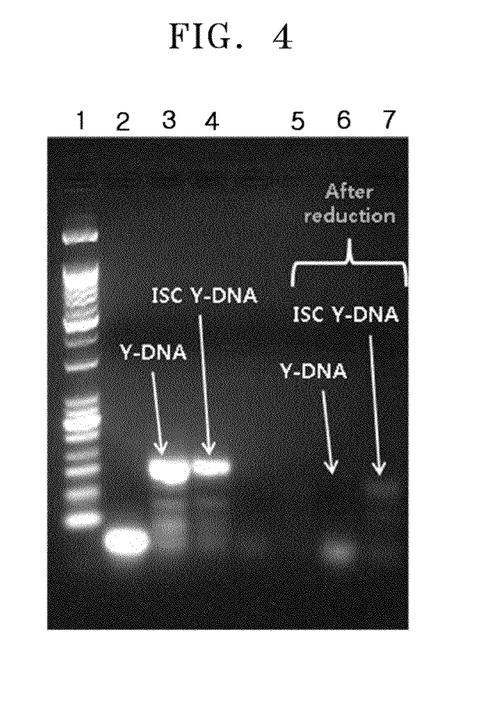
FIG. 4 illustrates electrophoresis results which confirm a Y-shaped nucleic acid template cross-linked by psoralen, according to an embodiment of the present invention (1: the marker lane, 2: lane 1, 3: lane 3, 4: lane 4, 5: lane 5, 6: lane 6, 7: lane 7)

FIG. 4 is an image showing electrophoresis results of the Y-shaped nucleic acid template for preparing a nanoparticle of Example 1 (Lane 3) and the nucleic acid template produced in Example 2 (Lane 4). In FIG. 4, the term "ISC Y-DNA" indicates a nucleic acid template conjugated with psoralen. As illustrated in FIG. 4, a band of the nucleic acid template with cross-linking between nucleic acid strands was more condensed than that of the Y-shaped nucleic acid template of Example 1, from which it is assumed that the Y-shaped nucleic acid template cross-linked by psoralen has a uniform shape.

EXAMPLE 3

Preparation of Y-Shaped Nanoparticle

The Y-shaped nucleic acid template for preparing a nanoparticle which had cross-linking between nucleic acid strands, prepared according to Example 2, and an aqueous HAuCl4 solution were mixed at a molar concentration ratio of 1:100 by stirring, and the resultant solution was then incubated at room temperature for 12 hours. Subsequently, the resultant mixture was filtered to remove unreacted Au ions therefrom and polynucleotides of the nucleic acid template with the Au ion bound thereto were suspended in distilled water. Thereafter, NaBH4 as a reducing agent was added to the resultant suspension at a molar concentration ratio of 1:10 and mixed together by stirring, and the resultant mixture was incubated at room temperature for 5 minutes to 1 hour. Afterwards, the resultant mixture was subjected to dialysis in water or a HCl solution was added thereto at a molar concentration ratio of 1:10, thereby completing the reducing process. As a result, a Y-shaped Au nanoparticle was obtained.

Figure 5:
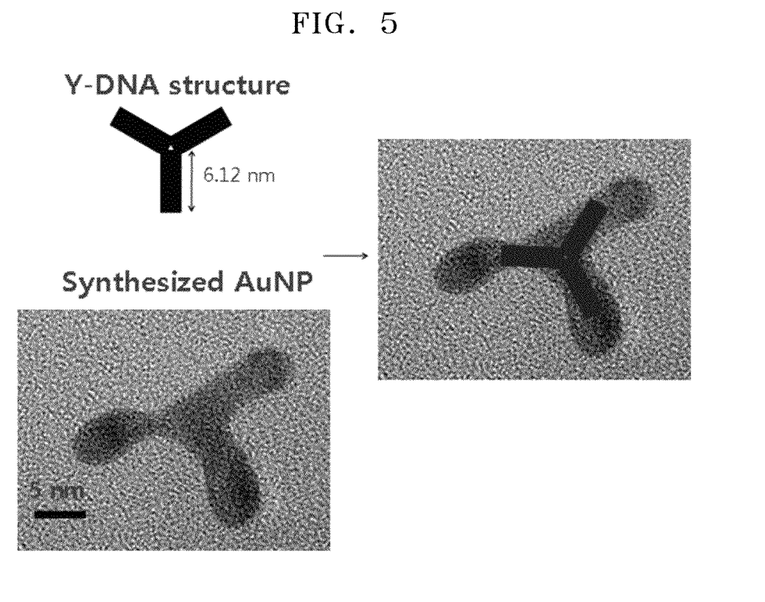
FIG. 5 is an electromicroscopic image of a Y-shaped gold nanoparticle prepared using a manufacturing method according to an exemplary embodiment of the present invention, in which the label "AuNP" means a gold nanoparticle.

The prepared Y-shaped Au nanoparticle was observed using UV/Vis spectroscopy and a transmission electron microscope (TEM). As shown in FIG. 5, the Y-shaped Au nanoparticle having a width of about 10 nm was confirmed.

Figure 6:
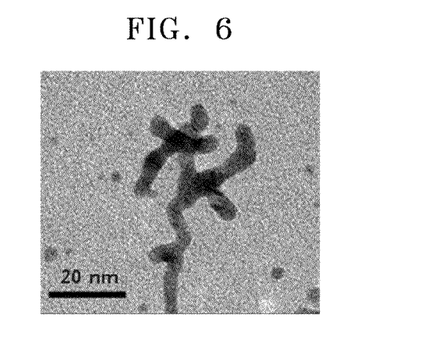
FIG. 6 is an electromicroscopic image of an X-shaped gold nanoparticle prepared using a manufacturing method according to an exemplary embodiment of the present invention.

In another embodiment, a TEM image of an X-shaped Au nanoparticle prepared in the same manner as in the preparation of the Y-shaped nucleic acid template described above is shown in FIG. 6. From these results, it is confirmed that various types of metal nanoparticles may be prepared in the same manner as Example 3 using various types of nucleic acid templates.

As described above, according to one or more of the above embodiments of the present invention, various types of metal nanoparticles may be efficiently prepared using templates for preparing nanoparticles and nanoparticles prepared using the templates.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A nanoparticle comprising a metal ion and a nucleic acid construct,
   wherein the nucleic acid construct comprises at least two single-stranded nucleic acids, each of the at least two single-stranded nucleic acids comprising at least ten nucleotides arranged in at least two adjacent segments, wherein each segment of one single-stranded nucleic acid is complementary to a segment of another of the single-stranded nucleic acids, and wherein each pair of complementary segments is hybridized so that the nucleic acid construct comprises a plurality of double-stranded segments; and
   wherein the metal ion is bound directly to a phosphate backbone of the nucleic acid construct to form a metal layer, and the metal ion is an ion of a metal selected from the group consisting of gold, copper, platinum, palladium, and combinations thereof,
   wherein the nucleic acid construct comprises at least one cross-linking or intercalating agent between two nucleic acid strands where the segments are substantially complementarily bound to each other.

2. The nanoparticle of claim 1, wherein the nucleic acid construct comprises 2 to 10 single-stranded nucleic acids.

3. The nanoparticle of claim 1, wherein each of the at least two single-stranded nucleic acids comprises 2 to 5 segments.

4. The nanoparticle of claim 1, wherein the nucleic acid construct comprises X-shaped, Y-shaped, liner, or a dumbbell-shaped double stranded segments.

5. A nanoparticle complex comprising at least two of the nanoparticles of claim 1, wherein an end of one of the at least two of the nanoparticles is bound to an end of the other thereof.

6. The nanoparticle complex of claim 5, wherein the nucleic acids are selected from the group consisting of deoxyribonucleic acid (DNA), ribonucleic acid (RNA), peptide nucleic acid (PNA), locked nucleic acid (LNA), and analogs thereof.

7. A method of preparing a nanoparticle, the method comprising:
   mixing at least two single-stranded nucleic acids each comprising at least two adjacent segments, wherein each segment of one single-stranded nucleic acid is complementary to a segment of another single-stranded nucleic acid, to give a nucleic acid construct in which the complementary segments are hybridized, and wherein the resulting nucleic acid construct comprises a plurality of double-stranded segments;
   adding an intercalator to a resultant of the hybridization and allowing the intercalator to be intercalated into the double-stranded segments;
   contacting the nucleic acid construct with a metal ion, wherein a the metal ion is an ion of a metal selected from the group consisting of gold, copper, platinum, palladium, and combinations thereof; and
   subjecting the metal ion to reduction to prepare a nanoparticle comprising the metal ion and the nucleic acid construct,
   wherein the metal ion is bound directly to a phosphate backbone of the nucleic acid construct to form a metal layer, and the metal ion is an ion of a metal selected from the group consisting of gold, copper, platinum, palladium, and combinations thereof,
   wherein the nucleic acid construct comprises at least one cross-linking or intercalating agent between two nucleic acid strands where segments are substantially complementarily bound to each other.

8. The method of claim 7, wherein the intercalator is selected from the group consisting of psoralen, ethidium bromide, proflavine, daunomycin, doxorubicin, thalidomide, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes, and 7-aminoactinomycin D.

9. The method of claim 7, wherein the nucleic acids are selected from the group consisting of deoxyribonucleic acid (DNA), ribonucleic acid (RNA), peptide nucleic acid (PNA), locked nucleic acid (LNA), and analogs thereof.

10. The method of claim 7, wherein the nucleic acid construct comprises 2 to 10 single-stranded nucleic acids.

11. The method of claim 7, wherein each of the at least two single-stranded nucleic acids comprises 2 to 5 segments.

12. The nanoparticle of claim 1, wherein the nucleic acid construct comprises three single-stranded nucleic acids, and wherein the three single-stranded nucleic acids are SEQ ID NO: 1, 2, and 3.

13. The nanoparticle of claim 7, wherein three single-stranded nucleic acids are mixed, and the three single-stranded nucleic acids are SEQ ID NO: 1, 2, and 3.

14. The nanoparticle of claim 1, wherein the cross-linking or intercalating agent is selected from the group consisting of psoralen, ethidium bromide, proflavine, daunomycin, doxorubicin, thalidomide, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes, and 7-aminoactinomycin D.

* * * * *

SEQUENCE LISTING

```
<160> NUMBER OF SEQ ID NOS: 3

<210> SEQ ID NO 1
<211> LENGTH: 36
<212> TYPE: DNA
<213> ORGANISM: Artificial Sequence
<220> FEATURE:
<223> OTHER INFORMATION: synthetic polynucleotide template for
      manufacturing Y-shape nanoparticle

<400> SEQUENCE: 1
cgagtaggta cggatctgcg tattgcgaac gactcg                               36

<210> SEQ ID NO 2
<211> LENGTH: 36
<212> TYPE: DNA
```

```
<213> ORGANISM: Artificial Sequence
<220> FEATURE:
<223> OTHER INFORMATION: synthetic polynucleotide template for
      manufacturing Y-shape nanoparticle

<400> SEQUENCE: 2
cgaccgatga atagcggtca gatccgtacc tactcg                              36

<210> SEQ ID NO 3
<211> LENGTH: 36
<212> TYPE: DNA
<213> ORGANISM: Artificial Sequence
<220> FEATURE:
<223> OTHER INFORMATION: synthetic polynucleotide template for
      manufacturing Y-shape nanoparticle

<400> SEQUENCE: 3
cgagtcgttc gcaatacgac cgctattcat cggtcg                              36
```